United States Patent [19]

Agar

[11] Patent Number: 5,263,363
[45] Date of Patent: Nov. 23, 1993

[54] APPARATUS AND METHOD FOR DETERMINING THE PERCENTAGE OF A FLUID IN A MIXTURE OF FLUIDS

[75] Inventor: Joram Agar, Grand Cayman, Cayman Islands

[73] Assignee: Agar Corporation, Ltd., Grand Cayman, Cayman Islands

[21] Appl. No.: 859,861

[22] Filed: Mar. 30, 1992

Related U.S. Application Data

[60] Continuation of Ser. No. 699,700, May 14, 1991, Pat. No. 5,101,367, which is a division of Ser. No. 311,610, Feb. 15, 1989, abandoned.

[30] Foreign Application Priority Data

Feb. 15, 1988 [GB] United Kingdom ................. 8803124

[51] Int. Cl.$^5$ .............................................. G01F 1/74
[52] U.S. Cl. ..................................................... 73/61.44
[58] Field of Search ................. 73/61.41, 61.43, 61.44, 73/61.61, 861.04

[56] References Cited

U.S. PATENT DOCUMENTS

| | | |
|---|---|---|
| 3,006,189 | 6/1956 | Warren et al. |
| 3,133,437 | 5/1964 | Remke et al. |
| 3,304,766 | 2/1967 | Hubby ............................. 73/61.44 |
| 3,385,108 | 6/1968 | Rosso |
| 3,774,448 | 11/1973 | Gass et al. ..................... 73/61.43 X |
| 4,266,188 | 5/1981 | Thompson |
| 4,340,938 | 7/1982 | Rosso ............................ 73/61.44 X |
| 4,429,273 | 1/1984 | Mazzagatti |
| 4,774,680 | 9/1988 | Agar ............................. 73/61.43 X |
| 4,873,648 | 10/1989 | Mouser et al. ................. 73/61.43 X |
| 4,916,940 | 4/1990 | Mougne ........................... 73/61.43 |
| 5,033,289 | 7/1991 | Cox ................................. 73/61.43 |
| 5,101,367 | 3/1992 | Agar ................................. 73/61.44 |

OTHER PUBLICATIONS

Kite, "Instrumentation for Simplified Commingling and Well-Testing Operations," Journal of Petroleum Technology, 1964, pp. 732-738.
Becher, "Emulsions: Theory and Practice", Second Edition, Reinhold Pub. Corp. NY, 1957, pp. 1-3, 84-95, 412-415.
Becher, "Physical Properties of Emulsions", pp. 49-94, Second Edition, Reinhold Pub. Corp., NY, Emulsions: Theory and Practice.
Becher, "Emulsions: Theory and Practice", pp. 151-208, Theory of Emulsions: Creaming, Inversion, and Demulsification.
Becher, "Emulsions: Theory and Practice", pp. 381-429, Testing of Emulsion Properties.
Bulletin of the Chemical Society of Japan, vol. 26, 1953, Tokyo, Japan, Kubo et al.

Primary Examiner—Hezron E. Williams
Assistant Examiner—Michael Brock
Attorney, Agent, or Firm—Oblon, Spivak, McClelland, Maier & Neustadt

[57] ABSTRACT

Disclosed is a method and apparatus for measuring the percentages of oil and water present in an oil/water mixture. By measuring the energy absorption properties of the oil/water mixture, the percentages of oil and water present in the oil/water mixture can be determined regardless of whether the oil or the water is in the continuous phase and regardless of what the relative proportions of water and oil are. Measuring the energy absorption properties of the oil/water mixture yields a current output which can be plotted on one of two distinct, empirically or theoretically derived data curves. One of the data curves represents oil being in the continuous phase and the other data curve represents water being in the continuous phase. A comparator is used to determine whether the oil or the water is in the continuous phase to thereby select the proper data curve on which the energy absorption is plotted. Each of the curves has the energy absorption properties of the media plotted against the percentage of water and plotting the amount of energy absorbed on the proper curve yields the percentage of water present.

4 Claims, 3 Drawing Sheets

APPARATUS AND METHOD FOR DETERMINING
THE PERCENTAGE OF A FLUID IN A MIXTURE
OF FLUIDS

CROSS REFERENCE TO RELATED APPLICATION

This is a continuation of application Ser. No. 07/699,700, filed on May 14, 1991, now U.S. Pat. No. 5,101,367 issued on Mar. 31, 1992, which is a division of U.S. application Ser. No. 07/311,610, filed Feb. 15, 1989, now abandoned.

FIELD OF THE INVENTION

The present invention relates generally to an apparatus and a method for determining the percentage of a fluid present in a mixture of fluids. Specifically, the present invention relates to an apparatus and a method for determining the percentage of oil or water in an oil/water mixture flowing through a predetermined region of a conduit.

BACKGROUND OF THE INVENTION

The accuracy of net oil measurement is extremely important to buyers and sellers of oil. If the oil contains water, the buyer does not want to pay for the oil on the basis of the gross amount of liquid shipped to him. Rather, he wants to pay only for the net amount of oil present in the total volume delivered. Net oil measurement is also required in oil fields for royalty payments and in enhanced oil recovery fields for pumping rate control.

There are in the art a number of instruments which have been used to measure water content in an oil/water mixture. Most of such instruments utilize the dielectric properties of the fluids, e.g., the difference between the dielectric constant of water and the dielectric constant of oil. As such, the main problem with such devices is their inability to operate with respect to mixtures where the water constituent of the mixture is in the continuous phase rather than the oil phase. By definition, the dielectric constant is the ratio of the capacitance of a capacitor field with a given dielectric to that of the same capacitor having only a vacuum as the dielectric. Therefore, in using the devices for oil continuous phase, the instrument will show a maximum value because the electric path between the two parallel plates of the capacitor will be shorted by the water in continuous phase. Unfortunately, this phenomena exists even though oil may still comprise a high percentage (e.g., some 40 or 50% or more) of the overall mixture.

Of the prior known devices, U.S. Pat. No. 4,774,680 to Agar is related to the present invention. The Agar patent addresses the problem of single curve characteristics. Agar solves the prior problem of determining a fundamental measurement based upon an electrical property of the fluid. Corrections to the fundamental measurement are not taught or suggested by the Agar patent.

A relatively typical capacitance probe for use in determining oil/water ratios is found in U.S. Pat. No. 3,200,312 to Callaghan. Callaghan relies on the measurement of the mixture's dielectric constant. As such, the probe must be non-functional when conductive water is in the continuous phase.

Yet another capacitance-type probe is taught in U.S. Pat. No. 3,025,464 to Bond. The Bond probe is designed specifically for pipeline use where there is typically low water content and oil is in the continuous phase. For that purpose, the Bond probe will function adequately. However, because the Bond probe is a capacitance probe, it will not function in mixtures where water becomes the continuous phase.

Still another prior art capacitance probe is shown in U.S. Pat. No. 3,523,245 to Love et al. It has the same shortcomings as the prior art references mentioned above. In fact, FIG. 2 of the Love et al. patent depicts a graph for water fraction versus probe capacitance. It is noted that the water fraction portion of the graph does not go above 0.5. In fact, the Love et al reference in discussing FIG. 2 specifally states that when the water fractions get above 0.5, the water tends to separate out and the capacitance quickly approaches the value at free water.

U.S. Pat. No. 3,368,147 to Graham teaches a capacitance measuring circuit to determine the sediment and water content of oil well production. Because Graham relies on capacitance, such reference is also insufficient to determine oil/water ratios where water is in the continuous phase.

U.S. Pat. No. 3,550,019 to Thomas seems to teach a linearizing circuit for net oil analyzers. However, Thomas does not teach the use of a digital linearizer or any means of overcoming the jump in the electrical characteristic of the mixture as the oil/water mixture moves from oil being in the continuous phase to water being in the continuous phase.

Yet another net oil computer is described in U.S. Pat. No. 3,385,108 to Rosso. Rosso relies on a capacitance probe and does not teach the use of a digital linearizer or any means of overcoming the jump in the electrical characteristic of the mixture when the oil/water mixture goes frm oil being in the continuous phase to water being in the continuous phase.

Another typical capacitance probe having the same inadequacies as those probes mentioned above is found in U.S. Pat. No. 3,006,189 to Warren et al.

A few techniques are available to measure the electrical properties of the mixture. For example, the conductivity of the mixture may be measured at a high frequency. While such techniques avoid the saturation effect which is typical of measuring capacitance, they produce two distinct, non-linear curves or families of curves of output signal. With the two distinct non-linear curves, the conductivity curves, the current may be plotted against the percentage of water in the mixture. The conductivity curves may be empirically or theoretically derived. The first set of these curves is for the case where the water is in the continuous phase, while the second set of these curves is for the case where oil is in the continuous phase. It should be understood that the "step jump" between these curves does not occur at a predetermined oil/water ratio. With respect to the "step jump" between the curves, other variables are involved including (as examples) the surface tension of the fluids and the amount of emulsifying chemicals present.

It is therefore a feature of the present invention to provide an apparatus and method for determining the percentage of water present in a mixture where either oil or water is in the continuous phase.

Yet another feature of the present invention is to provide an apparatus and method for determining the percentage of water in an oil/water mixture where the amount of water present is in the range from 0 to 100 percent.

Still a further feature of the present invention is to provide a method and apparatus for determining the water content in oil/water mixtures by measurement of the mixture's electrical properties wherein the output signal is linearized.

Still another feature of the present invention is to teach a method and apparatus for determining whether oil or water is in the continuous phase by measuring an electrical property of the mixture.

Yet a further feature of the present invention is to provide a method and apparatus for selecting one of two curves which represent the possible conditions of the media.

It is a further feature of the present invention to provide an apparatus and method for determining the percentages of oil and water in an oil/water mixture by measuring its electrical properties wherein it is determined whether the oil or the water is in the coninuous phase.

Yet another feature of the present invention is to provide two empirically or theoretically derived curves which plot percentage of water versus current which allows determination of whether the oil or the water is in the continuous phase.

Briefly stated, the foregoing and numerous other features, objects and advantages of the present invention will become readily apparent upon reading the detailed description, claims and drawings set forth hereinafter. These features, objects and advantages are accomplished by utilizing a microprocessor or comparator circuit which is able to distringuish between oil being in the continuous phase and water being in the continuous phase based on the electrical properties of the mixture. For example, the conductivity of the media may be measured at a high frequency. While these techniques avoid the saturation effect which is typical of measuring capacitance, they produce two distinct, non-linear curves of output signal typically plotting current versus the percentage of water in the mixture. These curves may be empirically or theoretically derived. The first of these curves is for the case where the water is in the continuous phase, while the second curve occurs where oil is the continuous phase. It should be understood that the change in phase does not occur at a predetermined oil/water ratio. Other variables are involved including droplet size, surface tension and emulsifying chemicals present. Typically however, the change occurs when the amount of water present in the mixture is in the range of approximately 35 to 75 percent of the total. Thus, just measuring the properties of the mixture does not give the complete solution. Because there are two distinct families of curves or equations it is necessary to determine which curve or equation is to be used in calculating the percentage of water present.

SUMMARY OF THE INVENTION

To achieve the foregoing objects, features, and advantages and in accordance with the purpose of the invention as embodied and broadly described herein, an apparatus and method for determining the percentage of a fluid in a mixture of fluids is provided. Among other advancements, the present invention is guided by the discovery that one of the variables is droplet size. The size of the droplets comprising the mixture has a marked effect on the apparent conductivity of the mixture and thus the energy absorbed. Droplet size has been found to be determined by the shearing velocity, i.e., the viscosity and the surface tension of the mixture. However, the most critical of the parameters is believed to be the velocity.

According, therefore, to the present invention, there is provided a method of determining the percentage of a fluid present in a mixture of fluids flowing through a predetermined region of a conduit. The method comprising obtaining a measurement of at least one electrical property of the mixture in the region, measuring the speed of flow of the mixture in the region, and employing the measurement and the speed of flow to apply a secondary correction to the fundamental measurement, to get an accurate percentage of the fluid present in the mixture of fluids irrespective of the droplet size or other characteristics of the mixture.

By way of example, the speed of flow of the mixture is used in the derivation of the correct percentage, by automaticly correcting for the effects of variation in the shape and size of the particles on the electrical property of the mixture. Preferably, the temperature of the mixture in the selected region is also obtained to apply one or more subsequent degrees of correction of the percentage of the fluid present in the mixture. Typically, velocity is the first degree correction.

Typically, the mixture can contain a mixture of a first and a second liquid. When an electrical property is plotted against the percentage, two data curves (or families of data curves) are obtained which curves are separated from each other. The two data curves represent the first liquid in the continuous phase and the second liquid in the continuous phase, respectively. The said first and second liquids may be water and oil, respectively.

The derivation of the percentage, preferably, involves determining whether the first or second liquid is in the continuous phase, selecting the appropriate data curve, and obtaining a reading from the latter. Preferably, the determination as to whether the first or second liquid is in the continuous phase is effected by comparing the measurement of the electrical property or properties to a predetermined value. Thereafter, one data curve or family of curves is selected when the measurement is above the predetermined value, and the other data curve or family of curves is selected when the measurement is below the predetermined value.

In the specific example of an oil/water mixture, the step jump from one family of curves to the other may occur when the amount of water in the mixture is in the range of approximately 35 to 75 percent of the total. Thus, just measuring the electrical properties of the mixture is not the complete solution because for the same percentage of mixture, a plurality of distinct values of electrical properties exist. Since there are two distinct sets of curves and respective equations to describe the curves, it is necessary to determine which curve or equation is to be used in calculating the percentage of water present.

As indicated above, the step jump occurs in the data when the mixture changes from oil being in the continuous phase to water being in the continuous phase. It is imperative to eliminate the step jump from the data and to linearize the two distinct curves or families of curves.

The step jump represents a rapid change in the conductivity of the mixture. This change in conductivity may be measured by a conductivity meter or energy absorption detector, typically for example, in the units of milliamps of output. Information concerning the change in conductivity may be used by a comparator to select one of two memories which are respectively programmed with data relating to water being in the continuous phase and to oil being in the continuous phase. By way of example, it has been determined that an oil/water monitor in a particular configuration measures a current of approximately less than 5 milliamps, when oil is in the continuous phase. Alternately, it has been determined that an oil/water monitor in a particular configuration measures a current of greater than approximately 5 milliamps, when water is in the continuous phase. The linearized output from the selected memory may be fed to an output stage, display or multiplier. The multiplier may be used to determine the net water content of the mixture by multiplying the gross flow rate by the percentage of water present. The difference between the gross flow rate and the net water content equals the net oil present.

In the above example, the characteristics of oil/water mixtures have been used as an example. There are however other physical examples of a distinct "jump" from one family of curves to another, i.e., a discontinuity in the function describing the physical phenomena. An example of such a discontinuous phenomena is the change from laminar flow to turbulent flow. The "jump" occurs in passing from laminar flow to turbulent flow at a Reynolds number of approximately 2000. The corrections practiced by the present invention can be applied to any such discontinuous functions.

According, therefore, to another aspect of the present invention, there is provided an apparatus for determining the percentage of a fluid present in a mixture of fluids flowing through a predetermined region of a conduit. The apparatus comprising electrical property or properties of the mixture in the region; flow measuring means for measuring the speed flow of the mixture in the region; and calculator means arranged to receive signals from the flow measuring means to apply a correction to the signal from the electrical property measuring means to calculate the correct percentage therefrom.

The apparatus preferably comprises temperature measuring means for measuring the temperature of the mixture in the region, the calculator means being arranged to receive signals from all said measuring means and to calculate the percentage therefrom. The calculator means may comprise memory means programmed with data relating to whether a first liquid or a second liquid of the mixture is in the continuous phase, the calculator means having data selection means arranged to select the data to be employed in calculating the percentage. The data selection means may comprise a comparator arranged to select the data to be employed in calculating the said percentage, the comparator comparing the said measurement with a predetermined value and selecting the data in accordance with whether the said measurement is above or below the predetermined value. The flow measuring means may be arranged to send a signal representative of flow through a conduit to a multiplier where the flow is multiplied by the percentage to produce an indication of the net flow of the fluid whose percentage has been calculated. A substractor may be provided for subtracting the last-mentioned net flow from the gross flow.

BRIEF DESCRIPTION OF THE DRAWINGS

The accompanying drawings which are incorporated in and constitute a part of the specification, illustrate a preferred embodiment of the invention and together with the general description of the invention given above and the detailed description of the preferred embodiment given below, serve to explain the principles of the invention. The invention is illustrated, merely by way of example, in the accompanying drawings, in which.

The above general description and the following detailed description are merely illustrative of the generic invention, and additional modes, advantages, and particulars of this invention will be readily suggested to those skilled in the art without departing from the spirit and scope of the invention.

DETAILED DESCRIPTION OF THE PREFERRED EMBODIMENTS

Reference will now be made in detail to the present preferred embodiments of the invention as described in the accompanying drawings.

The present invention is, in part, based on the discovery that the measurement of the conductivity or other electrical property of a mixture of fluids, such as an oil/water mixture, flowing through a predetermined region of a conduit is affected by the size and shape of the droplets of at least one of the liquids of the mixture, e.g., oil being in a continuous phase of another liquid of the mixture, e.g., water. This phenomena is illustrated in FIGS. 1 and 2.

Figure 1:
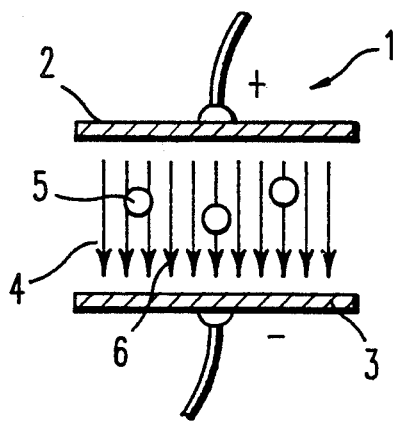
FIGS. 1 and 2 are illustrations of possible effects on the conductivity of an oil/water mixture, respectively, of large and small droplets.

In FIG. 1, there is shown diagrammatically a conductivity meter 1 having spaced apart positive and negative electrodes 2 and 3, respectively. An oil/water mixture 4 comprising 30% oil and 70% water flows through the space between the electrodes 2, 3. The mixture 4 is shown as having water in the continuous phase surrounding a plurality large oil droplets 5. The lines of force 6 between the electrodes 2, 3 are illustrated in FIGS. 1 and 2. As will be seen, a high proportion of the lines of force 6 are interrupted by the large oil droplets 5, so that the conductivity reading produced by the conductivity meter 1 will be below the true value.

Figure 2:
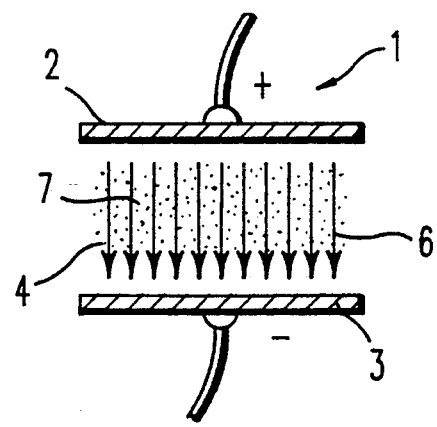

FIG. 2 is a view similar to FIG. 1, indicating the passage through the meter 1 with an oil/water mixture 4 comprising 30% oil and 70% water. In the FIG. 2 case, however, the mixture 4 contains a plurality of tiny oil droplets 7. As a result of the tiny oil droplets 7, the lines of force 6 are hardly affected and consequently the reading produced by the conductivity meter 1 will be above the true value.

Thus, although it is not obvious at first sight that the apparent conductivity of an oil/water mixture, which is flowing through a conduit and which has water in the continuous phase, is dependent upon the size, shape and distribution of the oil droplets, this is certainly the case. It has been found, indeed, that the apparent conductivity, and thus the energy absorbed by the fluid, is inversely proportional to the droplet size. Droplet size, as determined by the shearing velocity, is the most important of these factors.

Accordingly, the current (I) that is measured by the conductivity meter 1 as passing through the oil/water mixture 4 is a function (f) of the percentage of water (W) in the mixture 4 and the shearing velocity or velocity of flow (v) which is itself functionally related to the particle size.

Thus, $$I=f(W; v).  \quad (1)$$

Consequently, by measuring both the velocity of flow v and the current I, a set of simultaneous equations can be produced which can be solved to find the percentage of water W. The parameters of the calculations can be found empirically or by calculation.

A third parameter may also be needed if the temperature (T) of the measured mixture varies widely. Equation (1) then needs to be rewritten as $$I=f(W; v; T). \quad (2)$$

In order to solve equation (2), the temperature of the mixture 4 must be measured and three simultaneous equations must be solved.

Figure 3:
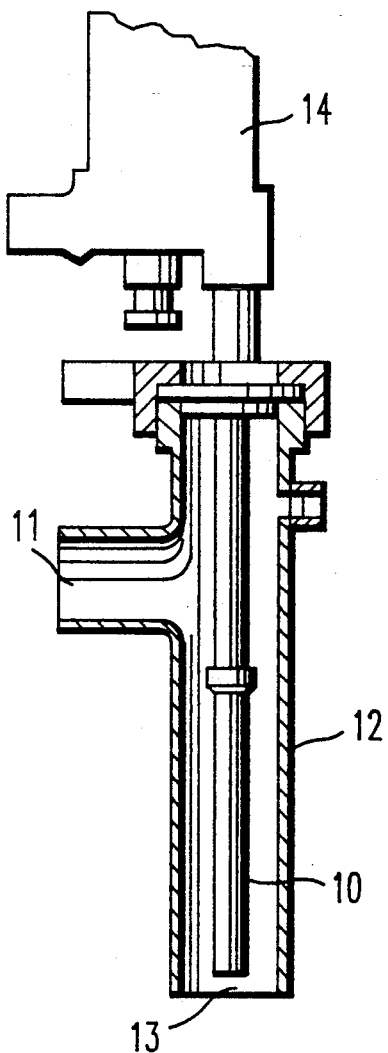
FIG. 3 is an elevation cross-sectional view of a preferred embodiment of an oil/water monitor which may be used in an apparatus practicing to the present invention.

Turning now to FIG. 3, there is shown therein a probe 10 mounted within a conduit 12. The conduit 12 has an inlet 11 through which an oil/water mixture passes into the conduit 12, the oil/water mixture passing out of the conduit 12 through an outlet end 13 of the latter. Energy is transmitted into the oil/water mixture in the conduit 12 from an oil/water monitor 14 and through the probe 10. In such manner, an oil/water monitor 14 can measure the electrical properties of the mixture flowing through conduit 12. This could, for example, be performed by measuring the conductivity, energy absorption capacitance, admittance and/or impedance of the oil/water mixture by means of the oil/water monitor 14. As used herein the term "electrical properties" includes all of such terms singly or in combination.

One such oil/water monitor 14, which can be used with the present invention, is the Agar Corporation OW-101 water in oil monitor as described in U.S. Pat. No. 4,503,383 to Agar et al.. The Agar OW-101 measures the energy absorption properties of the oil/water mixture, rather than just the capacitance thereof. It is programmed with an empirically generated curve in which current in milliamps is plotted against the percentage of water. The curve contains a pronounced step jump as the mixture goes from oil being in the continuous phase to water being in the continuous phase. Because the location of the step is affected by a number of variables, it can be difficult to determine precisely what percentage of water is present. Another device which may be used for oil/water monitor 14 is the Invalco Model No. CX-745-200 GP.

Figure 6:
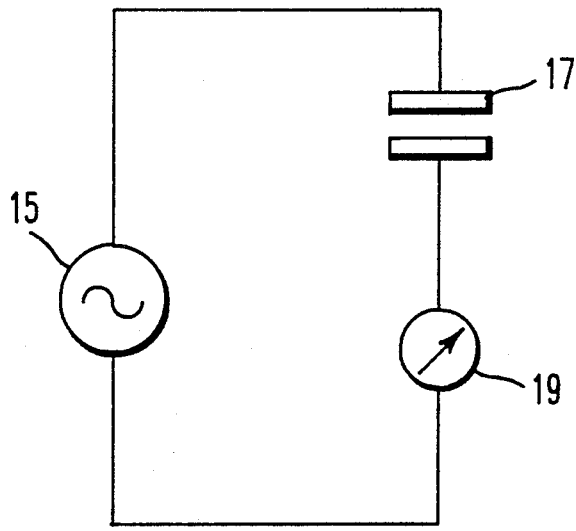
FIG. 6 is a schematic view of a circuit which may be used in an oil/water monitor forming part of an apparatus according to the present invention.

Still another device which can be used as an oil/water monitor 14 is shown schematically in FIG. 6. It includes an alternating current generator 15, a capacitor 17 and an ammeter 19. The capacitor 17 should be in the form of a probe which can be inserted into the oil/water mixture. The ammeter 19 measures current (I) so that when the water is in the continuous phase, the circuit can be defined by the equation:

$$I=V/R$$

which is Ohm's Law, where I is the current through the ammeter 19, V is the voltage of the generator 15, and R is the effective resistance of the oil/water mixture.

When oil is in the continuous phase, the circuit can be defined by the equation:

$$I=Vj\omega c$$

where "j" is the square root of $-1$, "$\omega$" represents the radial frequency and "c" represents the capacitance of the probe with the mixture inside it. Thus, there can be theoretically derived two distinct curves or equations representing some electrical property plotted against the percentage of water present.

It is known that the effective capacitance of a parallel plate capacitor is given by the equation:

$$C=KEA/D$$

where "C" is the effective capacitance, "K" is a dimensional constant, "E" is the dielectric constant of a medium such as an oil/water mixture between the plates of the capacitor, "A" is the area of the plates and "D" is the distance between the plates. It is further known that the effective resistance of a medium contained between the two plates of the capacitor is given by the equation:

$$R=D/AG$$

where "R" is the effective resistance, "D" is the distance between the plates, "A" is the area of the plates and "G" is the conductivity of the medium. Because both the dielectric constant and the conductivity of the medium are proportional to the percentage of water present in the medium, the derivation of two distinct equations is possible. However, the dielectric constant and conductivity of the medium depend not only on the percentages of water and oil present, but also on which constituent is in the continuous phase. As previously discussed, the constituent which is in the continuous phase is affected by a number of other variables. Therefore, in practice, it is typically simpler to use the empirically generated curves shown in FIG. 5.

Figure 4:
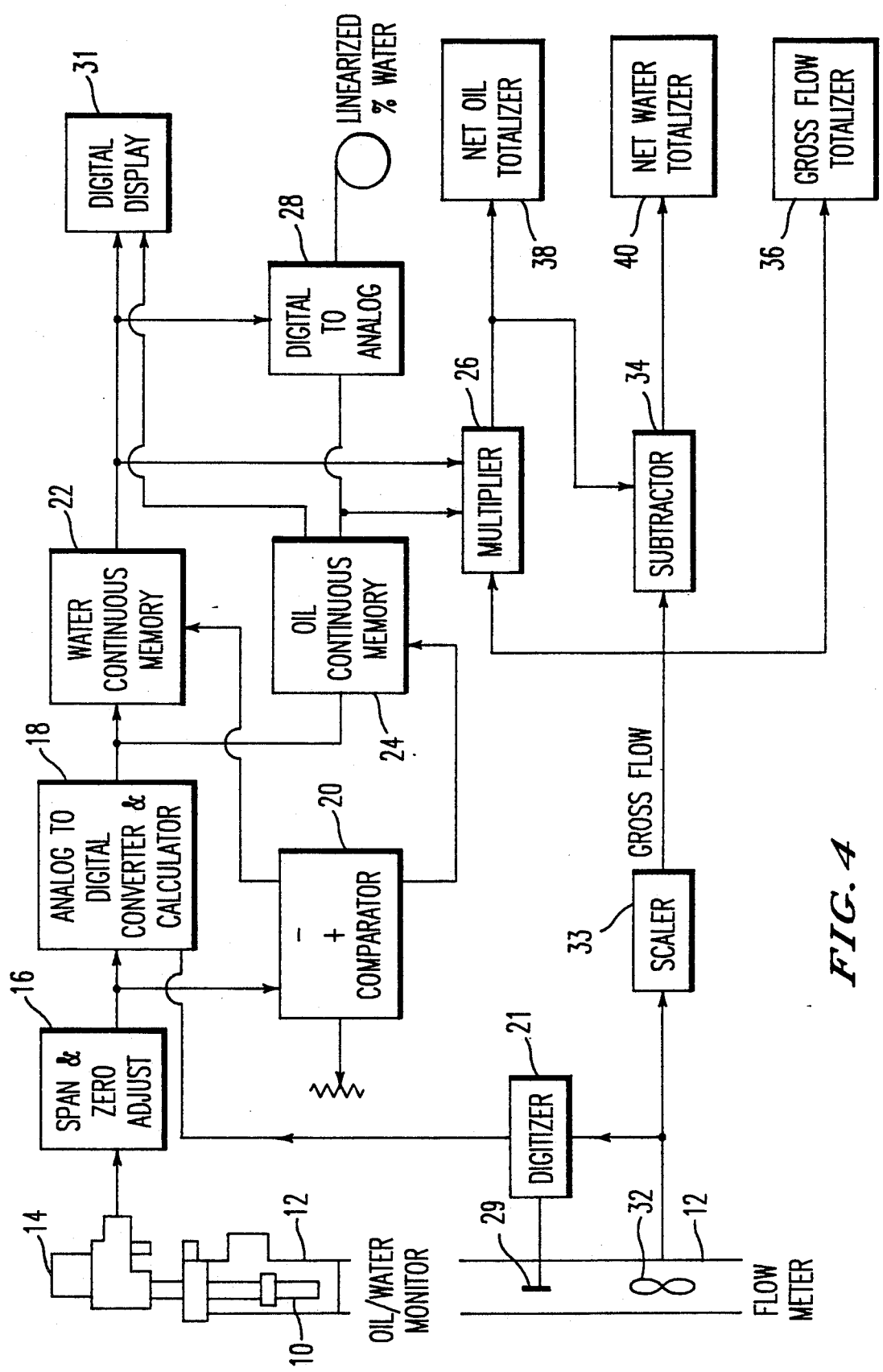
FIG. 4 is a schematic diagram of an embodiment of an apparatus according to the present invention.

The current or electrical signal generated in the oil/water monitor 14 is transmitted to a zero-and-span adjuster 16 (FIG. 4) which allows the apparatus to be calibrated. From the zero-and-span adjuster 16 the data is transmitted to an analog to digital converter and calculator 18 and to a comparator 20. The comparator 20 uses this information to select one or two memories, namely either a continuous water phase memory 22 or a continuous oil phase memory 24. The calculator 18 also receives a velocity signal "v" from a digitizer 21 which digitizes an analog signal received from a flow meter 32 in the conduit 12. Additionally, the digitizer 21, and consequently the calculator 18, may receive a temperature signal from a temperature measuring device 29 disposed in the conduit 12.

Figure 5:
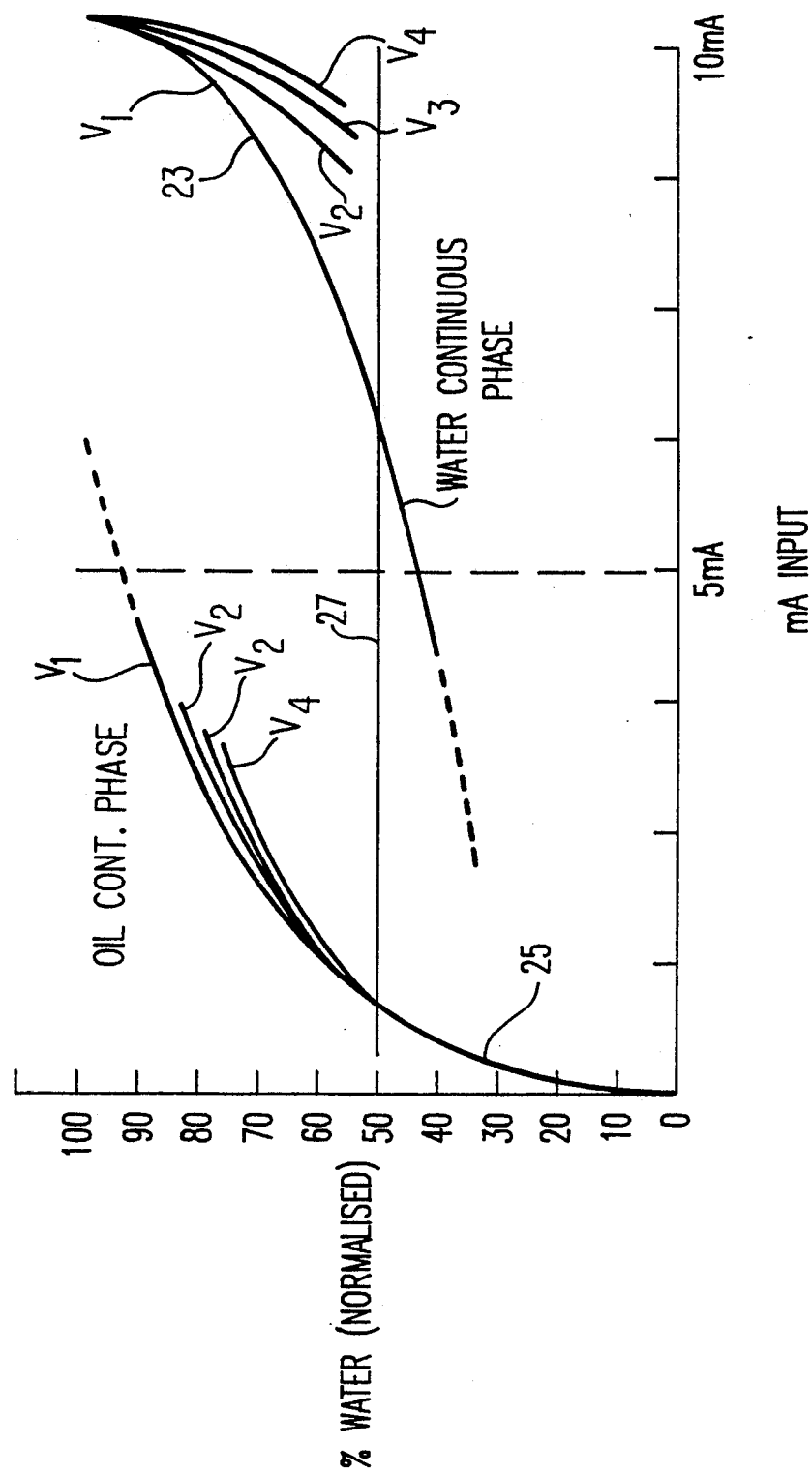
FIG. 5 is a graph of two empirically derived sets of curves in which current absorbed or admittance is plotted against the percentage of water in an oil/water mixture.

The continuous water phase memory 22 and the continuous oil phase memory 24 are programmed with families of curves 23 and 25, respectively, as shown in FIG. 5. As previously discussed, these curves can be arrived at empirically or theoretically. Curves 23 and 25 illustrate electrical signal plotted against the percentage of water present in the mixture at different flow velocities. The electrical signal may be in the form of a measurement of current, voltage, frequency, energy, conductivity, capacitance, admittance, impedance or the like. It should be recognized that the families of curves 23 and 25 represent two separate and distinct equations. It will be noted that the curves 23 and 25 have been projected, as shown by dotted lines, past the points where they intersect a step jump 27.

The comparator 20 will normally be a microprocessor or other computing device which compares the measured electrical signal shown in FIG. 5 as a current with a predetermined value, for example approximately 5 milliamps. If the measured current is greater than the predetermined value, then water is in the continuous phase and the comparator 20 selects the right hand set of curves 23. If the measured current is less than the predetermined value, then the oil is in the continuous phase and the comparator 20 selects the left hand set of curves 25.

The data transmitted from the oil/water monitor 14 provides the comparator 20 with the amount of current measured so that the comparator 20 can compare the measured value to the predetermined value. Depending on which continuous memory 22 or 24 is selected, the data is transmitted from the calculator 18 to that particular phase memory 22 or 24 where the amount of current is used to determine the percentage of water present by the way of the respective curve 23 or curve 25. The digitized data representing the percentage of water present is then transmitted to a multiplier 26 and, simultaneously, to a digital-to-analog converter 28. The data from the digital-to-analog converter 28 is then transmitted to a meter 30 where the percent of water can be directly read.

The flow rate of the oil/water mixture flowing through the conduit 12 is measured by the flow meter 32. The flow meter 32 is preferably a positive displacement type flow meter or some other high accuracy type flow meter. A signal from the flow meter 32 is transmitted simultaneously via a scaler 33 to the multiplier 26, a subtractor 34 and a gross flow totalizer 36. The gross flow totalizer 36 keeps a running tabulation of the total volume pumped through the conduit 12. The gross flow data transmitted from the flow meter 32 to the multipler 26 is multipled by the percentage of water data transmitted to the multiplier 26 from the memories 22 and 24. The data is then transmitted from the multiplier 26 simultaneously to a net water totalizer 38 and to the subtractor 34. The net water totalizer 38 keeps a running tabulation of the total amount of water which has been pumped through the conduit 12. Within the subtractor 34, the total water volume is substracted from the gross flow, the result being transmitted to the net oil totalizer 40. The net oil totalizer 40 keeps a running tabulation of the total volume of oil which has been pumped through the conduit 12.

The graph illustrated in FIG. 5 depicts a somewhat typical step jump 27 between the two non-linear sets of curves 23 and 25 which are generated when oil/water ratios are determined by measuring the electrical properties of the mixture. It is highly desirable to eliminate the step jump 27 from the data. It is also highly desirable to linearise the data. This is accomplished through the use of the comparator 20, the memories 22 and 24, and the calculator 18. Further, by relying on other electrical properties of the oil/water mixture such as energy absorption, rather than the dielectric constant alone, a measurement may be made of the ratio of oil to water regardless of which component is in the continuous phase up to and including the situation where there is no true mixture and 100 percent of the volume is water.

For purposes of clarification, the component in the continuous phase can be defined as that liquid which contains and surrounds the droplets of the second liquid such that the second liquid is present within the first liquid in the form of individual, discrete units.

What is claimed is:

1. An apparatus for determining relative amounts of oil and water in an oil/water mixture, comprising:
   probe means for monitoring a predetermined electrical property of said oil/water mixture and outputting corresponding measurement data;
   flow meter means for measuring flow of said oil/water mixture and outputting corresponding flow data;
   memory means for storing a first set of data curves of phase characteristics of said oil/water mixture in the oil continuous phase and for storing a second set of data curves of phase characteristics of said oil/water mixture in the water continuous phase;
   computer means for receiving the flow data from said flow meter means and the measurement data from said probe means and for outputting a selection signal to said memory means to select a data curve either from said first set or said second set based on the measurement data and the flow data, said memory means outputting output data derived from the selected data curve and corrected for the measured flow, said output data corresponding to said relative amounts of water and oil in the oil/water mixture; and
   display means for displaying an output related to said output data of said memory means.

2. The apparatus according to claim 1, further comprising:
   means for measuring temperature of the oil/water mixture and supplying temperature data to said computer means, said data curve being selected based in said flow data from said flow meter means, said temperature data from said temperature measuring means and said measurement data from said probe means.

3. An apparatus for determining a relative amount of oil and water in an oil/water mixture, comprising:
   probe means for monitoring a predetermined electrical property of said oil/water mixture and outputting corresponding measurement data;
   temperature means for measuring temperature of said oil/water mixture and outputting corresponding temperature data;
   memory means for storing a first set of data curves of phase characteristics of said oil/water mixture in the oil continuous phase and for storing a second set of data curves of phase characteristics of said oil/water mixture in the water continuous phase;
   computer means for receiving the temperature data from said temperature means and the measuring data from said probe means and for outputting a selection signal to said memory means to select a data curve either from said first set or said second set based on the measurement data and the temperature data, said memory means outputting output data derived from the selected data curve and corrected for the measured temperature, said output data corresponding to said relative amounts of water and oil in the oil/water mixture; and display means for displaying an output related to said output data of said memory means.

4. An apparatus for determining relative amounts of oil and water in an oil/water mixture comprising:

probe means for monitoring a predetermined electrical property in said oil/water mixture and outputting corresponding measurement data;

parameter measuring means for measuring at least one of flow and temperature of said oil/water mixture and outputting corresponding parameter data;

a computer including memory means for storing first and second equations representing phase characteristics of said oil/water mixture in the oil continuous phase and in the water continuous phase, wherein said parameter data and said measurement data are variables in said first and second equations, said computer receiving data from said probe means and said parameter means and selecting either said first equation or said second equation based on the measurement data and solving the selected equation utilizing the measurement data and the parameter data, said computer outputting output data derived from the selected equation and corrected for at least one of flow and temperature, said output data corresponding to the relative amount of water and oil in the oil/water mixture; and display means for displaying an output related to said output data of said computer.

* * * * *

UNITED STATES PATENT AND TRADEMARK OFFICE
CERTIFICATE OF CORRECTION

PATENT NO. : 5,263,363
DATED : NOVEMBER 23, 1993
INVENTOR(S) : JORAM AGAR

It is certified that error appears in the above-identified patent and that said Letters Patent is hereby corrected as shown below:

Column 1, line 45 "oil continuous" should read
--oil/water measurement, when water is the continuous--.

Signed and Sealed this

Twenty-eight Day of February, 1995

Attest:

BRUCE LEHMAN

*Attesting Officer*     *Commissioner of Patents and Trademarks*

EX PARTE REEXAMINATION CERTIFICATE (4935th)
United States Patent
Agar

(10) Number: US 5,263,363 C1
(45) Certificate Issued: *May 11, 2004

(54) APPARATUS AND METHOD FOR DETERMINING THE PERCENTAGE OF A FLUID IN A MIXTURE OF FLUIDS

(75) Inventor: Joram Agar, Grand Cayman (KY)

(73) Assignee: Agar Corporation Inc., Houston, TX (US)

Reexamination Request:
No. 90/004,943, Mar. 16, 1998
No. 90/005,963, Mar. 27, 2001

Reexamination Certificate for:
Patent No.: 5,263,363
Issued: Nov. 23, 1993
Appl. No.: 07/859,861
Filed: Mar. 30, 1992

(*) Notice: This patent is subject to a terminal disclaimer.

Certificate of Correction issued Feb. 28, 1995.

Related U.S. Application Data

(60) Continuation of application No. 07/699,700, filed on May 14, 1991, now Pat. No. 5,101,367, which is a division of application No. 07/311,610, filed on Feb. 15, 1989, now abandoned.

(30) Foreign Application Priority Data

Feb. 15, 1988 (GB) .............................................. 8803124

(51) Int. Cl.[7] ............................ G01F 1/74; G01N 27/02
(52) U.S. Cl. ..................................................... 73/61.44
(58) Field of Search .............................. 73/61.43, 61.41, 73/61.44, 61.61, 861.04; 702/22, 23, 24, 25, 100; 324/71.1, 698

(56) References Cited

U.S. PATENT DOCUMENTS 4,048,854 A * 9/1977 Herzl ...................... 73/861.04

OTHER PUBLICATIONS

Perl, "Complex Microwave Dielectric Properties of Liquids, Solutions, and Emulsions", Ph D. thesis, Illinois Institute of Technology, May 1984.*
Mansour, "Concentration Measurements in Emulsions", 22nd International Microwave Power Symposium: A Macro View of Microwaves and FR Heatins, Cincinnati, OH, Aug. 31–Sep. 2, 1987.*

* cited by examiner

Primary Examiner—Thomas P. Noland

(57) ABSTRACT

Disclosed is a method and apparatus for measuring the percentages of oil and water present in an oil/water mixture. By measuring the energy absorption properties of the oil/water mixture, the percentages of oil and water present in the oil/water mixture can be determined regardless of whether the oil or the water is in the continuous phase and regardless of what the relative proportions of water and oil are. Measuring the energy absorption properties of the oil/water mixture yields a current output which can be plotted on one of two distinct, empirically or theoretically derived data curves. One of the data curves represents oil being in the continuous phase and the other data curve represents water being in the continuous phase. A comparator is used to determine whether the oil or the water is in the continuous phase to thereby select the proper data curve on which the energy absorption is plotted. Each of the curves has the energy absorption properties of the media plotted against the percentage of water and plotting the amount of energy absorbed on the proper curve yields the percentage of water present.

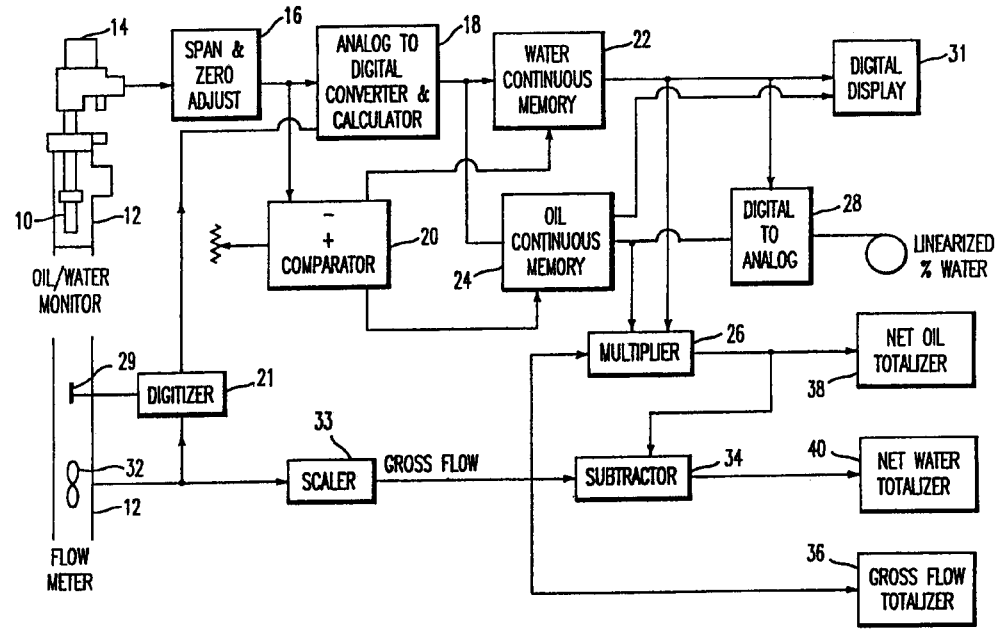

US 5,263,363 C1

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1 and 2 is confirmed.

Claims 3 and 4 are determined to be patentable as amended.

New claims 5–9 are added and determined to be patentable.

3. An apparatus for determining a relative amount of oil and water in an oil/water mixture, comprising:
  probe means for monitoring a predetermined electrical property of said oil/water mixture and outputting corresponding measurement data;
  temperature means for measuring temperature of said oil/water mixture and outputting corresponding temperature data;
  memory means for storing a first set of data curves of phase characteristics of said oil/water mixture in the oil continuous phase and for storing a second set of *overlapping* data curves of phase characteristics of said oil/water mixture in the water continuous phase;
  computer means for receiving the temperature data from said temperature means and the measuring data from said probe means and for outputting a selection signal to said memory means to select a data curve either from said first set or said second set based on the measurement data and the temperature data, said memory means outputting output data derived from the selected data curve and corrected for the measured temperature, said output data corresponding to said relative amounts of water and oil in the oil/water mixture; and
  display means for displaying an output related to said output data of said memory means.

4. An apparatus for determining relative amounts of oil and water in an oil/water mixture, comprising:
  probe means for monitoring a predetermined electrical property in said oil/water mixture and outputting corresponding measurement data;
  parameter measuring means for measuring at least one of flow and temperature of said oil/water mixture and outputting corresponding parameter data;
  a computer including memory means for storing first and second *overlapping* equations representing phase characteristics of said oil/water mixture in the oil continuous phase and in the water continuous phase, wherein said parameter data and said measurement data are variables in said first and second equations, said computer receiving data from said probe means and said parameter means and selecting either said first equation or said second equation based on the measurement data and solving the selected equation utilizing the measurement data and the parameter data, said computer outputting output data derived from the selected equation and corrected for at least one of flow and temperature, said output data corresponding to the relative amount of water and oil in the oil/water mixture; and
  display means for displaying an output related to said output data of said computer.

*5. An apparatus for determining a relative amount of oil and water in an oil/water mixture, comprising:*
  *a probe for monitoring a predetermined electrical property of said oil/water mixture and outputting corresponding measurement data;*
  *a flow measuring device capable of measuring the flow of an oil/water mixture and further capable of transmitting flow data indicative of the measured flow velocity or volume;*
  *a temperature measuring device for measuring temperature of said oil/water mixture and outputting corresponding temperature data;*
  *a memory for storing a first set of data curves of phase characteristics of said oil/water mixture in the oil continuous phase and for storing a second set of overlapping data curves of phase characteristics of said oil/water mixture in the water continuous phase;*
  *a calculating device coupled to said probe and said flow measuring device and capable of receiving measurement data from said probe and receiving flow data from said flow measuring device, said calculating device further being capable of selectively transmitting output data to said memory;*
  *a computer for receiving the temperature data from said temperature measuring device and the measuring data from said probe and for outputting a selection signal to said memory to select a data curve either from said first set or said second set based on the measurement data and the temperature data, said memory outputting output data derived from the selected data curve and corrected for the measured temperature, said output data corresponding to said relative amounts of water and oil in the oil/water mixture; and*
  *a display for displaying an output related to said output data of said memory.*

*6. The apparatus of claim 5, wherein said calculating device is coupled to said temperature measuring device and capable of receiving temperature data from said temperature measuring device.*

*7. The apparatus of claim 5, wherein said measurement data from said probe is one of (i) conductivity, (ii) energy absorption capacitance, (iii) admittance and (iv) impedance.*

*8. An apparatus for determining a relative amount of oil and water in an oil/water mixture, wherein the oil/water mixture is in a water continuous phase or an oil continuous phase, comprising:*
  *a probe for monitoring a predetermined electrical property in said oil/water mixture and outputting corresponding measurement data;*
  *a parameter measuring device for measuring at least one of flow and temperature of said oil/water mixture and outputting corresponding parameter data;*
  *a computer including memory for storing first and second overlapping equations representing phase characteris-* tics of said oil/water mixture in the oil continouous phase and in the water continuous phase, wherein said parameter data and said measurement data are variables in said first and second equations, said computer receiving data from said probe and said parameter measuring device and selecting either said first equation or said second equation based on the measurement data and solving the selected equation utilizing the measurement data and the parameter data, said computer outputting output data derived from the selected equation and corrected for at least one of flow and temperature, said output data corresponding to the relative amount of water and oil in the oil/water mixture;

a calculating device coupled to said probe and said parameter measuring device and capable of receiving said measurement data from said probe and receiving said parameter data from said parameter measuring device, said calculating device further being capable of selectively transmitting output data to said memory; and a display for displaying an output related to said output data of said computer.

9. The apparatus of claim 8, wherein said measurement data from said probe is one of (i) conductivity, (ii) energy absorption capacitance, (iii) admittance and (iv) impedance.

* * * * *